(12) United States Patent
Manor et al.

(10) Patent No.: US 6,719,698 B2
(45) Date of Patent: Apr. 13, 2004

(54) ULTRASONIC TRANSDUCER PROBE AND A MEASUREMENT DEVICE UTILIZING THE SAME

(75) Inventors: Dan Manor, Kadima (IL); Eli Levy, Ra'anana (IL); Roni Bibi, Herzelia (IL); Sergei Lukaschuk, Ra'anana (IL)

(73) Assignee: Cardiosonix Ltd., Raanana (IL)

( * ) Notice: Subject to any disclaimer, the term of this patent is extended or adjusted under 35 U.S.C. 154(b) by 0 days.

(21) Appl. No.: 09/907,439

(22) Filed: Jul. 18, 2001

(65) Prior Publication Data

US 2003/0018262 A1 Jan. 23, 2003

(51) Int. Cl.[7] ................................ A61B 8/02
(52) U.S. Cl. .................. 600/454; 600/446; 600/443
(58) Field of Search ....................... 600/437, 441, 600/446, 452, 454, 456, 459, 465, 468

(56) References Cited

U.S. PATENT DOCUMENTS

| | | | |
|---|---|---|---|
| 4,103,679 A | | 8/1978 | Aronson |
| 4,370,985 A | | 2/1983 | Takeichi et al. |
| 4,413,629 A | * | 11/1983 | Durley, III .................. 600/453 |
| 4,459,854 A | * | 7/1984 | Richardson et al. .......... 73/644 |
| 4,541,433 A | * | 9/1985 | Baudino ...................... 600/454 |
| 4,582,066 A | * | 4/1986 | Barnes et al. ............... 600/459 |
| 4,667,679 A | * | 5/1987 | Sahota ........................ 600/447 |
| 4,796,632 A | | 1/1989 | Boyd et al. |
| 5,119,821 A | * | 6/1992 | Tuchler ....................... 600/454 |
| 5,381,795 A | * | 1/1995 | Nordgren et al. ............ 600/472 |
| 5,575,289 A | | 11/1996 | Skidmore |
| 5,722,412 A | * | 3/1998 | Pflugrath et al. ............ 600/459 |
| 5,752,517 A | | 5/1998 | Harman et al. |
| 6,102,863 A | * | 8/2000 | Pflugrath et al. ............ 600/447 |

FOREIGN PATENT DOCUMENTS

| | | |
|---|---|---|
| EP | 0 150 672 A1 | 12/1984 |
| GB | 1439592 | 6/1976 |
| WO | WO 97/24986 | 1/1997 |

OTHER PUBLICATIONS

Skladany, Milan MD et al, New Angle–independent, Low––Cost Doppler System to Measure Blood Flow, The American Journal of Surgery, pp. 179–182, vol. 176, Aug. 1998, Excerpta Medica, Inc., U.S.A.

\* cited by examiner

Primary Examiner—Francis J. Jaworski
Assistant Examiner—William Jung
(74) Attorney, Agent, or Firm—Browdy and Neimark (57) ABSTRACT

A probe device is presented for use in an ultrasound-based measurement device for blood flow measurements in a patient's body. The probe comprises a housing containing a transducer arrangement. An outer surface of the housing, by which the probe is brought to a measurement location in the patient's body, is patterned so as to have at least one projecting portion. The design of the probe enables correct orientation of the transducers with respect to a blood vessel under measurements. The probe device is associated with an operation means for operating the probe, and an indication means for generating output data indicative of measurement results, which are incorporated in a common housing of a hand-held measurement device.

15 Claims, 7 Drawing Sheets

ULTRASONIC TRANSDUCER PROBE AND A MEASUREMENT DEVICE UTILIZING THE SAME

BACKGROUND OF THE INVENTION

The invention is generally in the field of ultrasound measurement techniques, and relates to an ultrasonic transducer probe for measuring the biological fluid flow within a vessel, and a measurement device utilizing such a probe. The invention is particularly useful for Doppler-based blood flow measurement and the determination of associated hemodynamic parameters.

BACKGROUND OF THE INVENTION

Ultrasonic probes are typically used for non-invasive measurements. When dealing with moving objects, such as blood in a patient's body, Doppler-based measurement techniques are typically used. These measurement techniques are generally of two types, utilizing, respectively, continuous and pulse transmission of ultrasonic waves.

U.S. Pat. No. 4,370,985 discloses a Doppler based ultrasound probe device for measuring blood flow rate and blood vessel diameter utilizing the continuous transmission of ultrasonic waves.

EP 0150672 discloses a process and device for determining the velocity and rate of flow of a fluid in a pipe by using a Doppler echographic method. Here, two mutually attached wave-train transmitter-receiver units are used and oriented with respect to a pipe such that the axis of one of the units is perpendicular to the axis of the pipe.

U.S. Pat. No. 4,103,679 discloses a Doppler based ultrasound system for blood flow measurement in a blood vessel. In this system, an ultrasound transducer array is used, being disposed relative to the blood vessel's longitudinal axis such that a pulse wave ultrasound beam emanating therefrom intercepts the blood vessel's longitudinal axis at a variable beam inclination angle θ. By this, blood flow can be quantitatively measured, independent of the beam inclination angle.

Other pulse-transmission based techniques are disclosed in the following publications: "*New, Angle-independent, Low-Cost Doppler System to Measure Blood Flow*" by M. Skladany et al., The American Journal of Surgery, Volume 176, August 1998, pgs. 179–182; and WO 97/24986.

Another technique based on the transmission of pulses of two ultrasound waves aimed at determining blood velocity is disclosed in WO 97/24986. This technique is based on the zero-crossing method for frequency measurement of Doppler shifts and the use of FM modulated or pulse signals with range clipping for localizing velocity measurements.

SUMMARY OF THE INVENTION

There is a need in the art to facilitate ultrasonic-based blood flow measurements by providing a novel probe device and a measuring device using the same.

The main idea of the present invention consists of providing a probe device of a specific design, which assists in orienting the probe device with respect to the blood vessel under measurement and in operating the probe device during measurement, and facilitates access of the ultrasound radiation to the blood vessel under measurement.

An ultrasonic probe device according to the invention is characterized by that an outer surface of the device, by which it is brought into contact with the patient's body, is patterned so as to have at least one projecting portion. A single tip-like projecting portion may be provided. This enables to manipulate the probe with respect to the patient's body so as to displace a muscle above the blood vessel, thereby minimizing ultrasound signal attenuation during measurements, and also to bring the transducer arrangement closer to the blood vessel.

The pattern may be in the form of two spaced-apart projections defining a recess (groove) therebetween. By using such a probe for measurements during a surgical operation (i.e., in a direct contact with a blood vessel under measurements), the blood vessel may be located within the recess, thereby stabilizing the measurements. The provision of such a recess-containing pattern also facilitates non-invasive measurements, for example, for dialysis grafts.

The probe dice may have a housing of a single-part design, or of a two-part design. In the case of the two-part design, one part is removably mountable onto the other part, and the pattern is formed on an outer surface of the removable part (by which the probe is brought into contact with tie patient's body). When the projection-recess pattern is made on the outer surface of the removable part of the housing, this part actually presents an adapter between the probe and the blood vessel. Various adapters with various pattern dimensions may be prepared, thereby enabling to select a suitable one to be mounted onto the transducers containing part of the housing.

A measurement device according to the invention for ultrasound-based blood flow measurements is characterized by that a probe unit and a control unit of the device are located adjacent to each other, the device thereby being a portable hand-held measurement device. Preferably, the probe unit and the control unit are incorporated in a common housing, e.g., shaped so as to be held like a pen. The control unit comprises probe operation means and indication means for generating signals indicative of the measurement results. The control unit may comprise a display, and/or a data processing and analyzing utility. Alternatively, or additionally, the measurement device is connectable to an external unit, having a display and/or such a data processing and analyzing utility. This design of the measurement device aids a user (physician) in monitoring and analyzing data during the measurements, and, if the above design of the probe is used, in orienting the probe along the longitudinal axis of the blood vessel under measurements.

There is thus provided, according to one aspect of the present invention, a probe device for use in an ultrasound measurement device, the probe device comprising a housing containing a transducer arrangement, an outer surface of the housing, by which it is brought into contact with the patient's body during operation, being patterned so as to have at least one projecting portion.

Preferably, the transducer arrangement comprises two transducers, each operating in transmitting and receiving modes. The transducers are preferably oriented with respect to each other such that first and second ultrasound beams produced by the first and second transducers, respectively, propagate along first and second beam propagation axes intersecting at a certain acute angle. Preferably, during the measurements, the probe is desirably positioned with respect to the blood vessel, such that each of the beam propagation axes intercepts the longitudinal axis of the blood vessel. This can be implemented by displacing the transducers with respect to the blood vessel, and performing preliminary measurements of the blood vessel diameter.

According to another aspect of the present invention, there is provided an ultrasonic transducer probe device for use in a measurement device for blood flow measurements in a patient's body, wherein:

the probe device comprises a housing containing a transducer arrangement;

an outer surface of the housing, by which it is brought to a measurement location in the patient's body, is patterned so as to have at least one projecting portion;

said transducer arrangement comprises first and second ultrasonic transducers, each operable in transmitting and receiving modes, the first and second transducers being oriented with respect to each other such that first and second ultrasound beams produced by the first and second transducers, respectively, propagate along first and second beam propagation axes intersecting at a certain acute angle.

According to yet another aspect of the present invention, there is provided an ultrasonic transducer probe device for use in a measurement device for non-invasive blood flow measurements in a patient's body, wherein:

the probe device comprises a housing containing a transducer arrangement;

an outer surface of the housing, by which the probe is brought into contact with the patient's body, is patterned so as to have a projecting tip-like portion, which, during manipulation of the probe with respect to the patient's body, enables to displace a muscle above a blood vessel under measurements.

According to yet another aspect of the present invention, there is provided an ultrasonic transducer probe device for use in a measurement device for non-invasive blood flow measurements in a patient's body, wherein:

the probe comprises a housing containing a transducer arrangement, an outer surface of the housing, by which the probe is brought into contact with the patient's body, is patterned so as to have a projecting tip-like portion, which, during manipulation of the probe device with respect to the patient's body, enables to displace a muscle above a blood vessel under measurements;

the transducer arrangement comprises first and second ultrasound transducers, each operable in transmitting and receiving modes, the first and second transducers being oriented with respect to each other such that first and second ultrasound beams produced by the first and second transducers, respectively, propagate along first and second beam propagation axes intersecting at a certain acute angle;

According to yet another aspect of the present invention, there is provided a probe device for use in an ultrasound measurement device for measuring a blood flow condition in a patient's blood vessel, wherein:

the probe comprises a housing containing a transducer arrangement;

the housing is composed of first and second parts, the second part being removably mountable onto the first part, an outer surface of said second part, by which the probe is brought into contact with the blood vessel during measurements, having a pattern defining a recess for locating the blood vessel therein.

According to yet another aspect of the present invention, there is provided a probe device for use in an ultrasound measurement device for measuring a blood flow condition in a patient's blood vessel, wherein:

the probe comprises a housing containing a transducer arrangement;

the housing is composed of first and second parts, the second part being removably mountable onto the first part, an outer surface of said second part, by which the probe is brought into contact with the blood vessel during measurements, having a pattern defining a recess for locating the blood vessel therein;

said transducer arrangement comprises first and second ultrasonic transducers, each operable in transmitting and receiving modes, the first and second transducers being oriented with respect to each other such that first and second ultrasound beams produced by the first and second transducers, respectively, propagate along first and second beam propagation axes intersecting at a certain acute angle.

In a measurement device according to the invention, the probe device and a control unit are located adjacent to each other, preferably being incorporated in a common pen-like housing. The control unit comprises at least an operation means for operating the probe device (including user's interface, e.g., keys, and electronic components), and an indication means, and may also comprise a display and/or data processing and analyzing utility. By this, a user (physician) can use the probe in the most convenient manner (without a need to move his eyes away from the measurement site).

Thus, according to yet another aspect of the present invention, there is provided a hand-held measurement device for ultrasound-based measurements of a blood flow in a patient's body, the device comprising an ultrasonic transducer probe device and a control unit accommodated in a common housing, the control unit comprising an operation means for operating the probe and an indication means for generating data indicative of measurement results.

A preferred measurement technique consists of the following: once the probe is desirably positioned, measurements are carried out consisting of insonating the blood vessel with two pulse-wave ultrasound beams, in a manner to substantially simultaneously (in comparison to the physiological time scale) obtain multiple sample volumes at successive coordinates (gates) along each of the beam propagation axes. In other words, for each of the beams, the reflection amplitude with Doppler shifted frequency is measured as a function of sample volume position along the ultrasound beam axis, and is represented in the sampled form as an n-element vector where the i-th element is an instantaneous value of reflection amplitude for a particular gate. By applying the complex demodulation technique, which utilizes the synchronous multiplication of this real vector of reflection amplitudes on two periodic functions with 90°-shift in phase and with the frequency equal to that of the transmitted radiation, and applying a low pass filtering, the n-element vector of complex values (I & Q) for each of the beam is obtained. By this, the central spectral frequency of the complex vector is shifted from that of the ultrasound pulse towards zero frequency. By repeating the ultrasound pulses transmission/receiving procedure m times, an n×m two-dimensional matrix $E_{ij}$ of reflection amplitude values is obtained for each of the beams. Here, i is the gate coordinate index (i=1, . . . ,n) and j is the time coordinate index (j=1, . . . ,m). It should be understood that each of the reflection amplitude values is complex and indicative of the amplitude and the phase of the reflection at the respective gate at a certain time. By processing and analyzing these matrices (for two beams), the diameter of the blood vessel can be calculated, as well as the dynamic characteristics of the blood flow, such as Doppler shifts, inclination angles, velocity, and velocity profile along the ultrasound beam.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
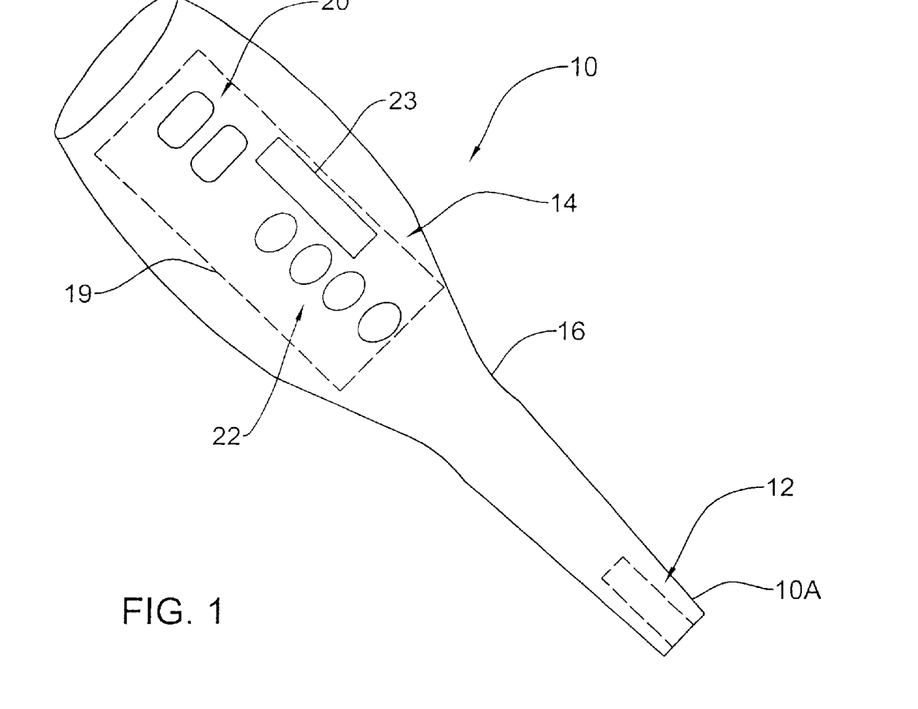
FIG. 1 schematically illustrates a moment device according to the invention for blood flow measurements in a patient's blood vessel.

Referring to FIG. 1, there is illustrated a measurement device 10 according to the invention for blood flow measurement in a blood vessel (e.g., carotid artery), and the determination of associated hemodynamic parameters. The measurement device 10 includes such main constructional parts as an ultrasonic probe 12 located at a distal end 10A of the device, and a control unit 14, which are incorporated in a common housing 16. The housing 16 is shaped so as to be held like a pen, so as to enable handling of the device by a user (physician) during measurements.

In the present example, the control unit 14 comprises a control panel 19 having operation keys 20 (e.g., press buttons) for operating the probe, an indication means 22 (which may be audio, e.g., beeper and/or visual, e.g., LEDs), a display 23 (for displaying the measurement results), and corresponding electronic components, which will be described more specifically with reference to FIG. 3. The indication means serves for providing an indication of the probe positioning during the measurements, as will be described more specifically further below. The device 10 is connectable to an external unit (not shown) including a data processing and analyzing utility. Such an external unit may be provided with a display (for displaying the measurement results) accommodated so as to be viewed by the user. It should be noted that, generally, the data processing and analyzing utility may be partly or completely incorporated in the hand-held device 10. The location of the control panel adjacent to the probe facilitates the measurement procedure.

Figure 2A:
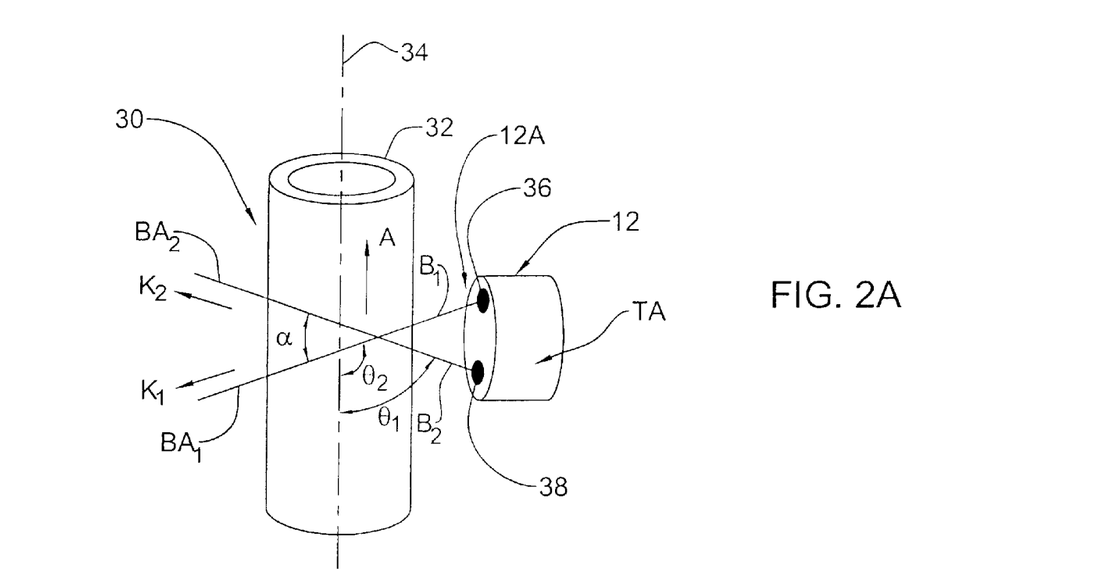
FIGS. 2A and 2B illustrate a probe of the measurement device of FIG. 1 applied to a blood vessel, showing two different orientations of the probe, respectively, with respect to the blood vessel.
Figure 2B:
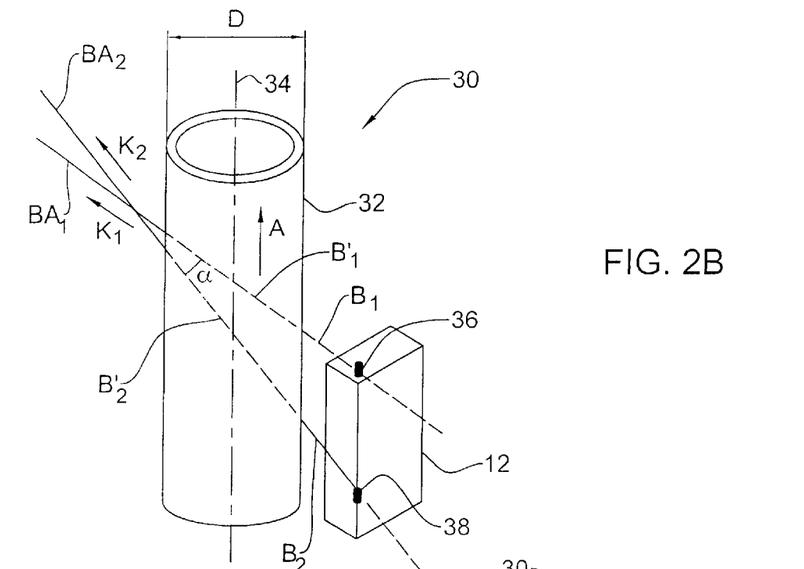

Referring to FIGS. 2A and 2B, the patient's blood vessel 30 is schematically shown as a right cylindrical duct through which blood flows in a direction denoted A. The blood vessel 30 has a wall 32, a longitudinal axis 34, and a diameter D. The probe 12 comprises a transducer arrangement TA mounted at the distal end 12A of the probe. The transducer arrangement comprises a pair of ultrasound transducers 36 and 38 operated for transmitting and receiving a pair of narrow pulse wave (PW) multi-gated ultrasound beams $B_1$ and $B_2$ having a pair of ultrasound beam propagation axes $BA_1$ and $BA_2$, respectively. The transducers 36 and 38 are oriented with respect to each other so as to ensure that the beam axes $BA_1$ and $BA_2$ intercept at an acute intersection angle $\alpha$.

The preferred measurement technique is such that, during the measurements, the transducers 36 and 38 are to be oriented with respect to the blood vessel 30 so as to ensure that each of the beams' propagation axes $BA_1$ and $BA_2$ crosses the longitudinal axis 34 of the blood vessel. This means that the beams' axes and the longitudinal axis of the blood vessel lie in a common plane. This can be achieved by appropriate displacement of the transducers with respect to the blood vessel. To this end, the entire probe (i.e., the entire device 10) can be manipulated. Alternatively, the construction may be such that one transducer is displaceable with respect to the other, for example, utilizing a specific support assembly disclosed in WO 00/28899 assigned to the assignee of the present application.

In the example of FIG. 2A, the probe 12 has an elongated shape. The transducers 36 and 38 are oriented with respect to the blood vessel 30 such that the components of their ultrasound wave vectors $k_1$ and $k_2$ along the vessel axis 34 are of opposite signs, which means also the opposite signs of Doppler shifts for beams $B_1$ and $B_2$. For example, if the configuration is such that the angle $\alpha$ between the beam propagation axis is equal to 60° and the probe surface (through which the ultrasound beam propagate towards the blood vessel) is parallel to the vessel, then acute beam inclination angles $\theta_1$ and $\theta_2$ subtended by the ultrasound beams $B_1$ and $B_2$, respectively, with the longitudinal axis 34 of the blood vessel are: $\theta_1=60°$ and $\theta_2=120°$. In the example of FIG. 2B, the transducers are oriented such that the components of their wave vectors $k_1$ and $k_2$ along the vessel axis are of the same sign, and corresponding Doppler shifts are negative for both beams.

Each of the above two different transducer arrangements provides additional flexibility for probe positioning, and the most suitable one of them could be chosen by a physician to meet the requirements of specific measurement conditions. The use of the configuration of FIG. 2A is preferred in the case when the blood vessel to be measured is positioned directly under the probe tip. The use of the configuration of FIG. 2B is preferred in the case when a measurement location is shifted ahead from the probe tip, and the access to the blood vessel is complicated by shadowing from a muscle or bone.

Figures 2C, 2D:
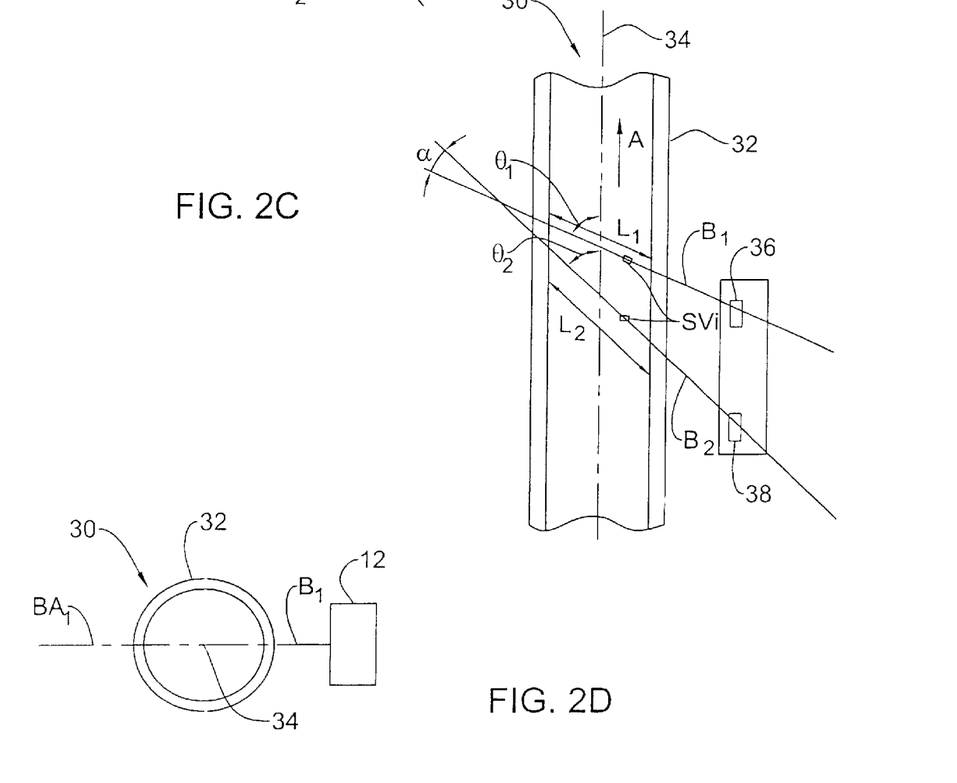
FIGS. 2C and 2D more specifically illustrate the ultrasound beams' propagation with respect to the longitudinal axis of the blood vessel, when the probe is positioned properly relative to the blood vessel, with the probe configuration of FIG. 2B.

As better seen in FIGS. 2C and 2D, the axes $BA_1$ and $BA_2$ of the multi-gated ultrasound beams $B_1$ and $B_2$ intercept at an acute intersection angle $\alpha$, and intercept the longitudinal axis 34 of the blood vessel at angles $\theta_1$ and $\theta_2$. A correct positioning of the transducers with respect to the blood vessel is such that each of the intercepting beam propagation axes $BA_1$ and $BA_2$ crosses the longitudinal axis 34 of the blood vessel. As indicated above, this may be achieved by the manipulation of the entire device with respect to the blood vessel (or displacement of one transducer with respect to the other) with simultaneous preliminary measurements of the blood vessel diameter. These preliminary diameter measurements utilize an algorithm of blood vessel boundary detection, which is the same for the examples of FIGS. 2A and 2B. The user manipulates the probe, and when the correct positioning is obtained, a certain indication signal is read from the device 10.

Thus, the ultrasound transducers 36 and 38 can be moved together by manipulating the probe 12 to ensure that the beam propagation axes $BA_1$ and $BA_2$ intercept the blood vessel's longitudinal axis 34. Turning back to FIG. 2B, there is shown that, at such transducers' positioning, the ultrasound beams $B_1$ and $B_2$ subtend the acute beam inclination angles $\theta_1$ and $\theta_2$ (where $\theta_1=\theta_2+\alpha$), respectively, with the longitudinal axis 34, and have beam portions $B_1'$ and $B_2'$ (shown in dashed lines) of lengths $L_1$ and $L_2$, respectively, which transverse the blood vessel at diametrically opposite portions of the vessel.

Figure 3:
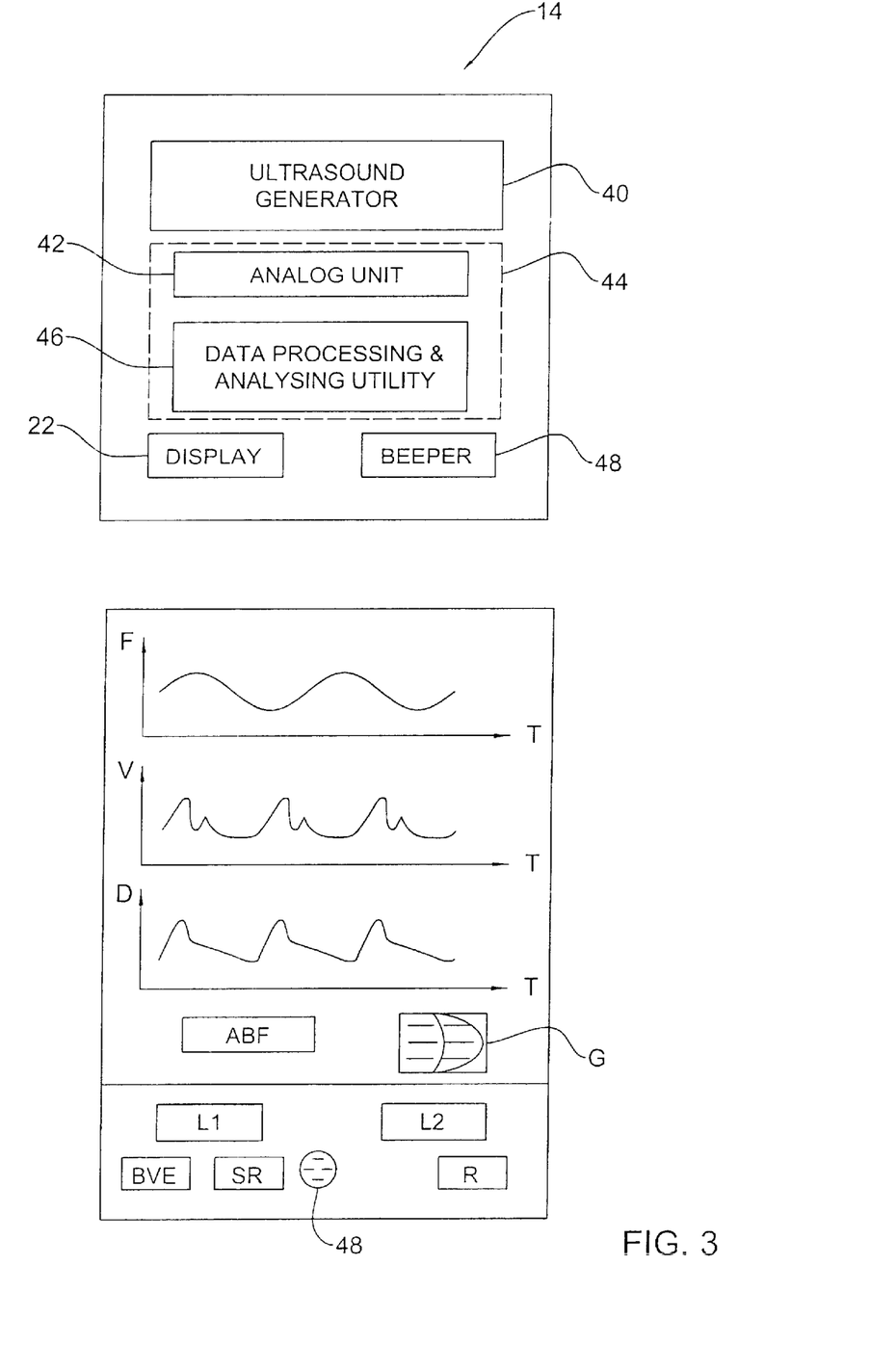
FIG. 3 illustrates the main constructional parts of a control unit suitable to be used in the device of FIG. 1A.

Turing now to FIG. 3, the control unit 14 comprises an ultrasound generator 40 for energizing the ultrasound transducers and a processor 44. As indicated above, the processor 44 may be part of the external device. The processor 44 includes an Analog unit 42 and a data processing and analyzing utility 46. The Analog unit is operable for signal amplification, complex demodulation and digitizing at a predetermined number of sample volumes ($SV_j$ in FIG. 2C) along each of the ultrasound beams. The data processing and analyzing utility 46 is operable for receiving and analyzing measured data and generating data indicative of flow related information to be displayed on a display of the external device or of the hand-held device 10. As shown, the displayed data may include the following: the two values $D_1$ and $D_2$ (related to the first and second beams, respectively); a graph of the blood flow against time, i.e., F(T); a graph of the blood velocity against time, i.e., V(T); a graph of the blood vessel diameter against time, i.e., D(T); a graph G of representative systolic and diastolic blood flow velocity profiles; average blood flow value ABF over a cardiac cycle; an index of blood vessel elasticity BVE over a cardiac cycle; shear rate SR; and a time dependent distal resistance index $R_s(T)$.

The values $D_1$ and $D_2$ are preferably diameters of the vessel measured by two transducers. Alternatively, when using another configuration, $D_1$ and $D_2$ could be the maximal values of velocities measured at the centers of the respective beams' intersections with the blood vessel, i.e., chords. As shown in the present example of FIG. 3, the indication means include an audio indication utility 48 (a beeper) for issuing indication signals when the optimal position of the probe is being reached, to thereby facilitate the manual set-up of the measurement device.

For the best representation of the blood flow velocity as a function of time, a location of a corresponding gate should be determined. This location is determined as the center of the lengths (blood vessel's chords) $L_1$ and $L_2$ for the two beams, respectively. The technique of the present invention allows for automatically defining the best location for determining and displaying the time dependence of the blood flow velocity, immediately after the determination of the chords.

Figure 4A:
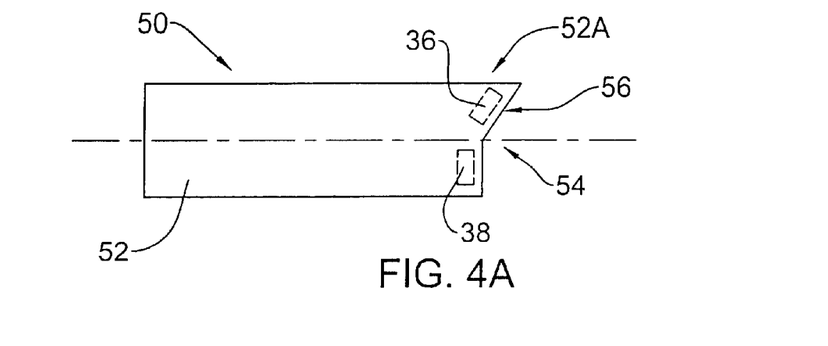
FIGS. 4A, 4B and 4C illustrate two examples of the probe according to the invention.
Figure 4B:
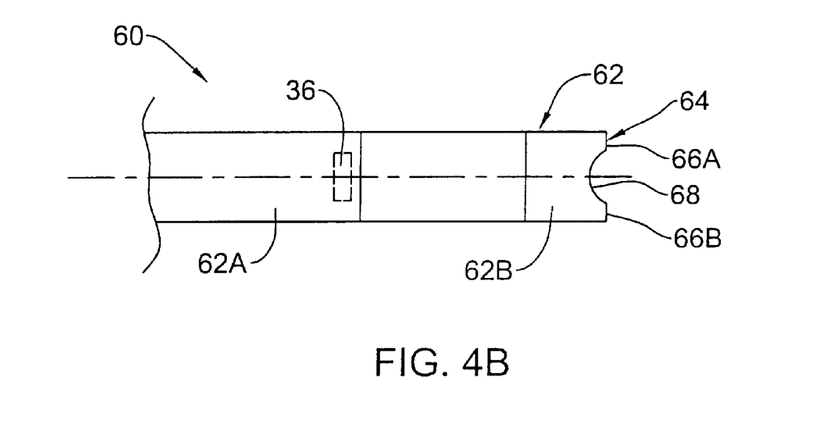
Figure 4C:
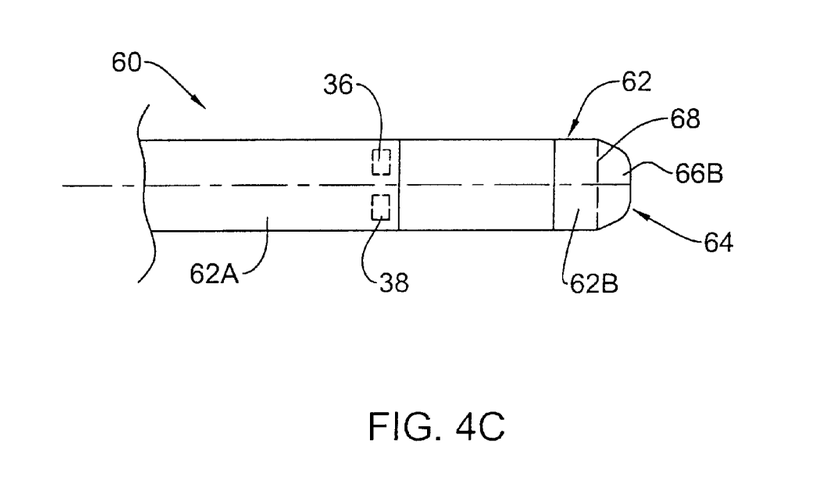

Reference is made to FIGS. 4A–4C, wherein FIG. 4A and FIGS. 4B–4C show, respectively, two examples of the probe device according to the invention.

In the example of FIG. 4A, a probe device 50 has a sine-part elongated housing 52, the transducer arrangement (transducers 36 and 38) being mounted inside the housing at a distal end 52A thereof. An outer surface 54 of the housing (at the distal end thereof), by which it is brought into contact with the patient's body, is patterned. The pattern is in the form of a surface relief defining a projecting tip-like portion 56. The provision of the tip-like portion 56 enables to manipulate the probe so as to "displace" a muscle layer above the blood vessel under measurements to thereby minimize ultrasound signal attenuation during measurements. This stabilizes the measurements and makes them more accurate. As further shown in the figure, by locating one transducer 36 within the projecting portion 56 and the other transducer 38 within the substantially flat portion perpendicular to the longitudinal axis of the housing, the desired orientation of the propagation axes of ultrasound beams (namely, to intercept with each other at a known angle) is provided.

In the example of FIGS. 4B–4C, a probe device 60 has a two-part housing 62, wherein the transducers 36 and 38 are mounted inside the first part 62A of the housing at a distal end thereof, and the second part 62B of the housing presents an adapter for adapting the probe to a specific blood vessel to which measurements are to be applied. The second part 62B is removably mountable onto the distal end of the first part 62A, and has a patterned (surface relief) outer surface 64, by which the probe is to be brought into contact with the patient's blood vessel. Here, the pattern is in the form of two spaced-apart projections 66A and 66B defining a recess 68 therebetween. When the probe 60 is put in operation, a blood vessel is located in the recess 68. A set of such adapters 62B can be prepared with different patterns, namely, different sizes of the recess 68 (and, optionally, different sizes of the projections 66A and 66B), thereby allowing a user (physician) to select a suitable one of the adapters to be mounted onto the housing part 62A. The location of the blood vessel under measurements within the recess 68 stabilizes the measurements.

It should be noted, although not specifically shown, that the transducers 36 and 38 may be accommodated inside the adapter-part 62B, the other part 62A serving as a holder of the probe. However, by locating the transducers in the first part 62, the second, adapter-like part 62B, by which the device contacts the patient's body, may be disposable. This design of the probe allows the user to quickly position the probe such that the two beam propagation axes lie in the common plane with the longitudinal axis of the blood vessel, and that a desired angle between the beam propagation axes and the blood vessel is provided.

The measurement device (10 in FIG. 1) operates in the following manner. A user brings the device into contact with the patient's body, and puts it in operation by actuating a corresponding key on the control panel. If measurements are to be applied non-invasively, e.g., on the patient's carotid artery, femoral artery, etc., the probe design 50 (with a tip-like projecting portion) is preferably used and is brought into contact with the patent's tissue adjacent to the artery. The user manipulates the device to ensure that both ultrasound beams $B_1$ and $B_2$ transverse the blood vessel at substantially but typically not diametrically opposite portions of the vessel wall 32. The ultrasound generator 40 energizes the ultrasound transducers 36 and 38 to transmit the pair of narrow PW ultrasound beams $B_1$ and $B_2$. The Analog unit 42 measures the Doppler frequency shift within each of a discrete series of small sample volumes $SV_1$ along each of the ultrasound beams $B_1$ and $B_2$. The processor 44 detects that the probe is correctly positioned with respect to the blood vessel and the beeper 48 generates an indication signal. The processor 44 determines the initial beam corrected chord lengths $L_1$ and $L_2$ (the same as vessel diameters $D_1$ and $D_2$) of the beam portions $B_1'$ and $B_2'$ (as will be described below with respect to the ultrasound beam $B_1$ only for the sake of convenience) or central chord velocities, and presents their values on the display (either of the device 10 or of the external device). The user may note the initial values $D_1$ and $D_2$ to manipulate the device to "search" for the maximum values $D_1$ and $D_2$ which is indicative of that the transducers are correctly positioned with respect to the blood vessel, namely, the beam propagation axes $BA_1$ and $BA_2$ cross the longitudinal axis of the vessel. Practically, the user manipulates the device until the indication signal is provided.

Figure 5:
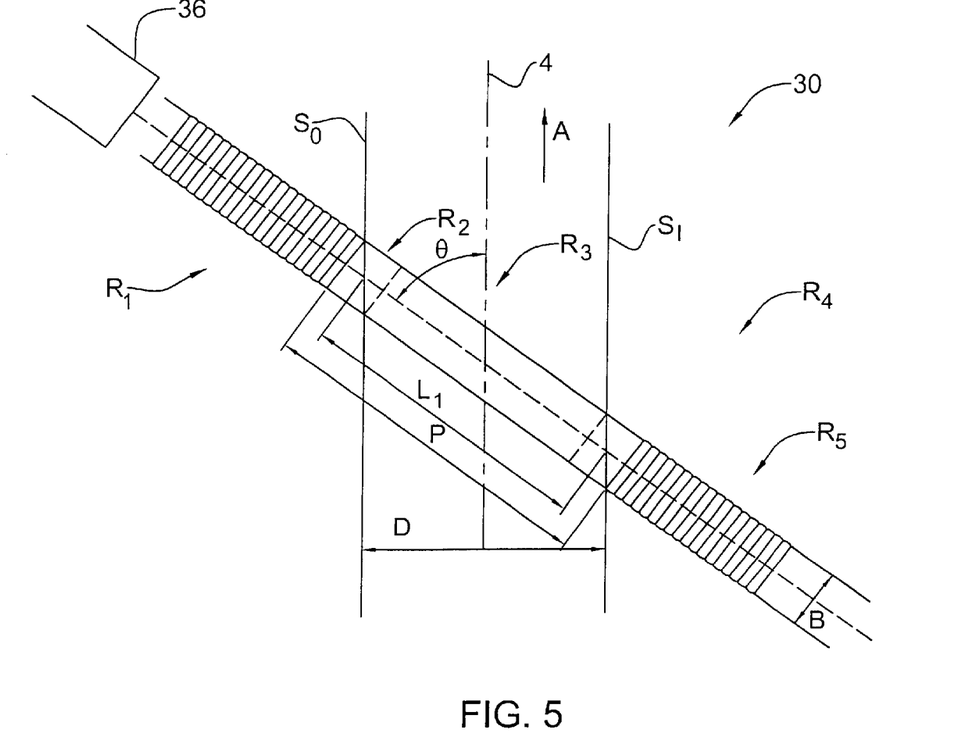
FIG. 5 schematically illustrates the ultrasonic beam propagation through the blood vessel according to a measurement technique of the present invention.

In the present example, the transducers are operated in a pulsed mode to obtain 220 gates along each ultrasound beams $B_1$ and $B_2$. The number of gates is a parameter selected at the stage of system initialization and depends on the resolution, central frequency and penetration depth of ultrasound. FIG. 5 shows the propagation of the ultrasound pulse along beam $B_1$ produced by the transducer 36, but it should be understood that the similar beam propagation is simultaneously provided (in physiological time scale) by the other transducer. Thus, the same number of gates (220 gates in this specific example) along each of the ultrasound beams can be divided into five distinct regions as follows:

a first region $R_1$ closest to the ultrasound transducer 36 and consisting of consecutive gates (1,85), which are wholly exterior to the blood vessel;

a second region $R_2$ consisting of consecutive gates (86, 90) which partially intercept the outermost surface $S_O$ of the blood vessel's wall 32 closest to the ultrasound transducer 36;

a third region $R_3$ consisting of consecutive gates (91,155) wholly within the blood vessel;

a four region $R_4$ consisting of consecutive gates (156,160) which partially intercept the innermost surface $S_I$ of the blood vessel's wall 32 furthermost from the ultrasound transducer 36; and a fifth region $R_5$ furthermost from the ultrasound transducer 36 consisting of consecutive gates (161,220), which are wholly exterior to the blood vessel.

What is actually measured is a chord length P of the three intermediate regions $R_2$, $R_3$ and $R_4$. This measured chord length P is used for determining the beam corrected chord length L according to the relationship: $L=P-B/\tan\theta$, where B is the width of the ultrasound beam, and $\theta$ is the acute beam inclination angle subtended between the ultrasound beam axis $B_1A_1$ and the blood vessel's longitudinal axis 34.

Determination of the beam corrected chord length L is in principle a two step process, consisting of the following:

calculation of a 220-component real vector of time averaged amplitude values $E_i$ from a 220×m matrix of complex reflections amplitude values $E_{ij}$ acquired over m excitations of the ultrasound transducer 36, wherein m defines the averaging time and could be adjusted with respect to the noise level (m is preferably equal to $2^k$, wherein k is integer, m=64 is a preferable default value); and detection of the first and last gates along the ultrasound beam $B_1$, which intercept with the outermost surface $S_O$ and the innermost surface $S_I$ of the blood vessel's wall 34, and which are respectively adjacent the ultrasound transducer 36 and remote therefrom.

The calculation of the 220-component real vector involves the high pass filtering of the columns of the 220×64 matrix of complex reflections amplitude values $E_{ij}$ along the time coordinate (second matrix index) for removing spurious low frequency noise and reflections from unmovable objects, and thereafter performing either frequency domain operations or time domain operations. The high pass filtering procedure is associated with the fact that the high frequency signals are associated with moving objects, namely, blood within the blood vessel, and therefore enables to define the blood vessel walls.

Figure 6:
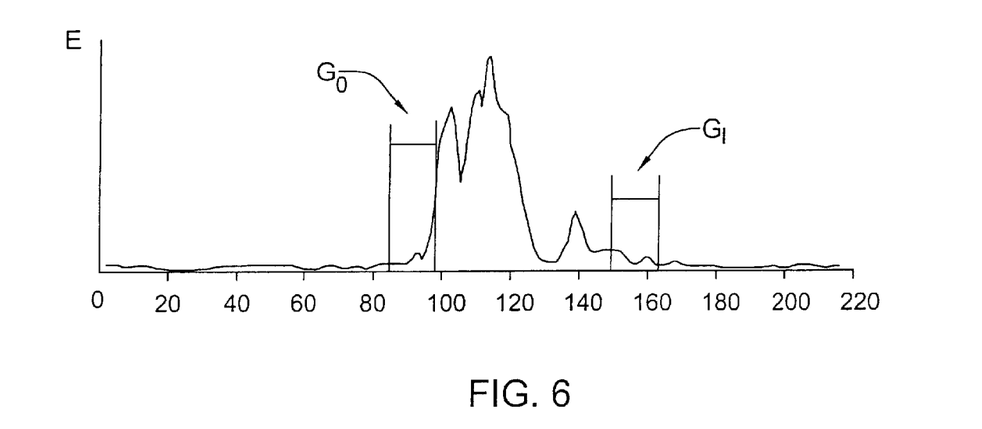
FIGS. 6–9 and 10A–10C graphically illustrate the measurement technique used in the present invention.

The frequency domain operations include executing a complex Fast Fourier Transform (FFT) on the 220×64 two-dimensional matrix of reflection amplitudes $E_{ij}$, summing the resulting complex spectral amplitudes $I_{ij}$ for each column (j=1, . . . , 64) of the 220×64 complex matrix $I_{ij}$ resulting from the FFT according to the relationship:

$$\sum_{j=1}^{m}\sqrt{(Iij_{Real})^2+(Iij_{Image})^2}$$

and repeating the summation operation for each gate (i=1, . . . , 220) along the ultrasound beam $B_1$ so as to obtain a vector of 220 energy values $E_i$ shown graphically in FIG. 6.

The time domain operations include summing the real amplitudes' values $E_{ij}$ for each column (j=1, . . . , 64) of the 220×64 matrix of complex reflections amplitude values $E_{ij}$ according to the relationship:

$$\sum_{j=1}^{m}\sqrt{(Eij_{Real})^2+(Eij_{Image})^2}$$

and repeating the summation operation for each gate (i=1, . . . , 220) along the ultrasound beam $B_1$ so as to obtain the 220-component vector of time averaged reflection amplitude values $E_i$. Alternatively, either the real part only or the imaginary part only of the matrix $E_{ij}$ for each column (j=1, . . . , 64) of the 220×64 two-dimensional matrix $E_{ij}$ can be summed.

On the basis of the vector of 220 values $E_i$, two approaches can be employed for determining the measured chord length P as follows: parametric estimation involving the detection of the first and last parabolic like portions along the vector $E_i$, or, alternatively, thresholding techniques. Parametric estimation is carried out by examining consecutive groups of 20 consecutive gates along the ultrasound beam $B_1$, thereby specifying 200 consecutive groups therealong, and includes the following steps: calculating the coefficients a, b and c of the equation:

$y=a+bE_i+cE_i^2$ for 200 groups of consecutive gates (i, i+20) for i=1 to 200; calculating an identification value $T_{left}$ of the innermost boundary (leftmost in the figure) according to the relationship:

$$T=\frac{c}{\sqrt{(a^2+b^2)}}$$

for each group of 20 consecutive gates; and determining the group of consecutive gates, denoted $G_O$, closest to the ultrasound transducer 36 which has the maximum $T_{left}$ value of the 200 $T_{left}$ values (see FIG. 6). Of this group of consecutive gates $G_O$, the outermost surface $S_O$ of the blood vessel's wall 34 is assumed to be the group's fist gate closest to the ultrasound transducer 36 which, in this specific example, is the gate 85 bordering between the regions $R_1$ and $R_2$. These steps are then repeated for the gates along the ultrasound beam $B_1$ in the reverse direction for determining the group of consecutive gates with the maximum outermost boundary (rightmost in FIG. 6) identification value $T_{right}$, which are again 200 $T_{right}$ values denoted $G_I$ (see FIG. 6). Of this group of consecutive gates $G_I$, the innermost surface $S_I$ of the blood vessel's wall 34 is assumed to be the group's last gate furthermost from the ultrasound transducer 36 which, in this example, is the gate 165 bordering between the regions $R_4$ and $R_5$.

One thresholding algorithm involves selecting all gates along the ultrasound beam $B_1$ (and along the other beam as well) which satisfy the conditions $E_i \geq AADTE$ and $E_i \geq AATE$ where the value of the so-called "average absolute derivative threshold energy" (AADTE) of the vector of 220 values $E_i$ is calculated according to the relationship:

$$AADTE = \frac{1}{n}\sum_{i=1}^{n} |E_{i+1} - E_i|$$

and the value of the so-called "average amplitude threshold energy" (AATE) of the vector of 220 values $E_i$ is calculated according to the relationship:

$$AATE = \frac{\text{mean of } E_i \text{ values} + \text{median of } E_i \text{ values}}{2}$$

Figure 7:
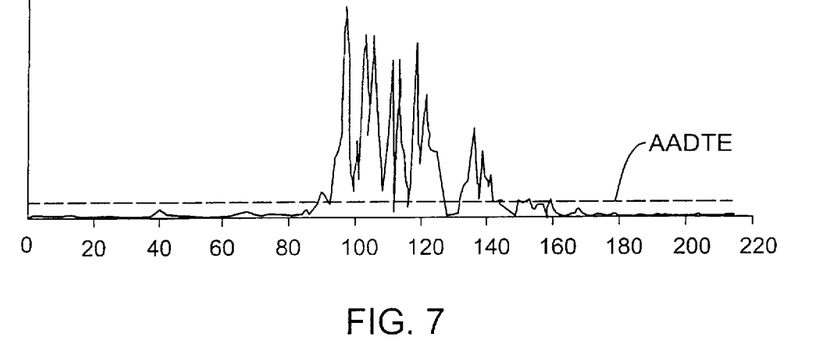
Figure 8:
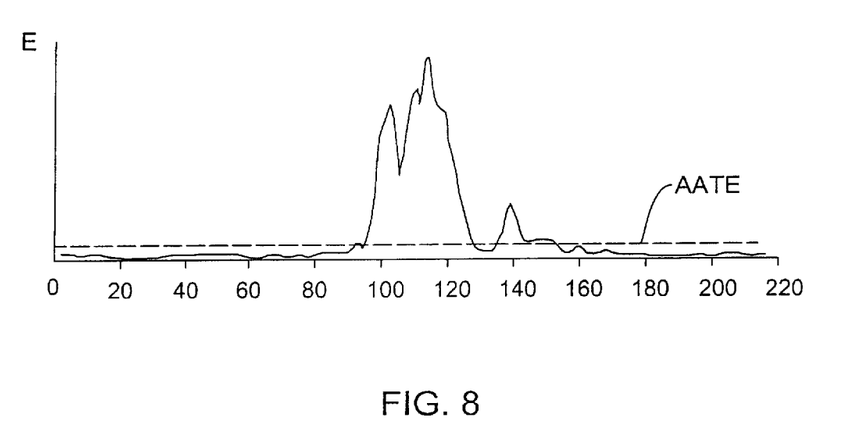

FIG. 7 graphically shows the gates along the ultrasound beam $B_1$ whose derivative energy values exceed the value of an AADTE parameter. FIG. 8 graphically shows the gates along the ultrasound beam $B_1$ whose energy values $E_i$ exceed the value of an AATE parameter.

Figure 9:
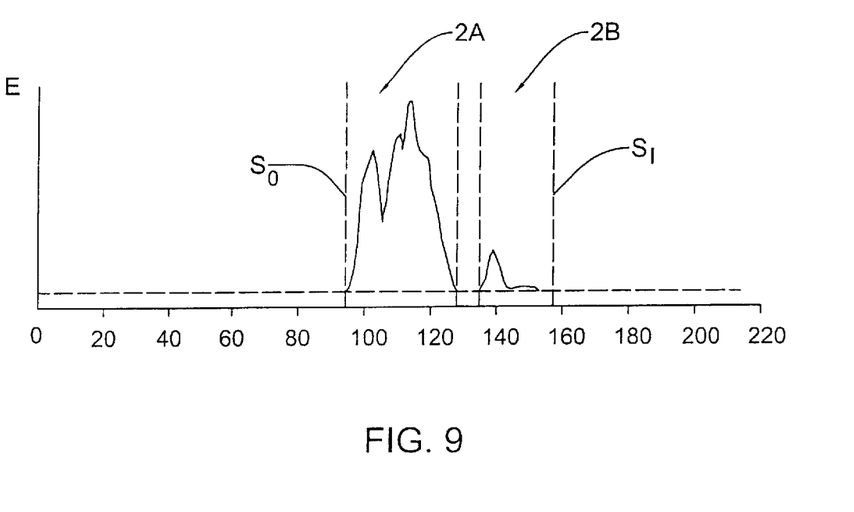

This approach may render so-called multiple humped graphs ostensibly, indicating the presence of several phantom blood vessels. As shown in FIG. 9, a pair of such phantom blood vessels $V_1$ and $V_2$ must be necessarily combined to render a single blood vessel. This can be achieved by the following algorithm:

generating a g single dimension vector K of all the gates (i=1 to 220) along the ultrasound beam whose energy value $E_i$ satisfies the conditions $E_i \geq AADTE$ and $E_i \geq AATE$;

generating a h single dimension vector DK where $DK_h = K_{h+1} - K_h$ for h=1 to g;

calculating the parameter Average DK according to the relationship:

$$\text{Average } DK = \frac{1}{g}\sum_{h=1}^{g} DK_h$$

determining the innermost region of gates which satisfies the condition $DK_h/2 \geq$ Average DK, and specifying that the innermost gate of the innermost region is the outermost surface $S_O$; and determining the outermost region of gates which satisfies the condition $DK_h/2 \geq$ Average DK, and specifying that the rightmost gate of the rightmost region is the innermost surface $S_I$.

For example, for a vector $DK_h = [1,1,1,1,1,1,3,1,1,4,1,1,1,1,]$, Average DK=19/14, the so called innermost region is where DK=3, the so-called outermost region is where DK=4, the innermost gate of the innermost region DK=3 is the outermost surface $S_O$, and the outermost gate of the outermost region DK=4 is the innermost surface $S_I$.

Figure 10A:
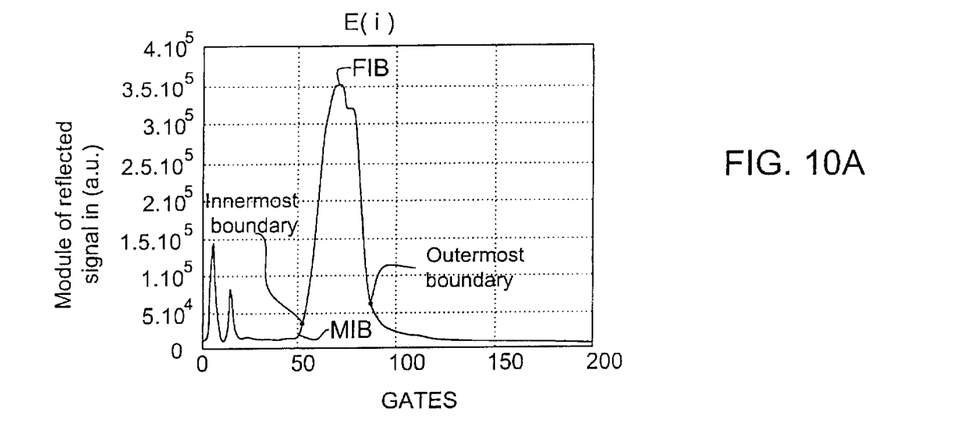
Figure 10B:
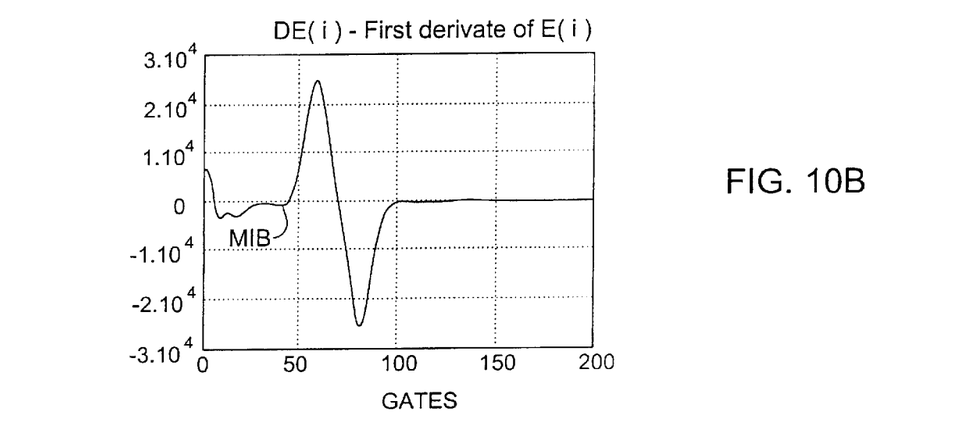
Figure 10C:
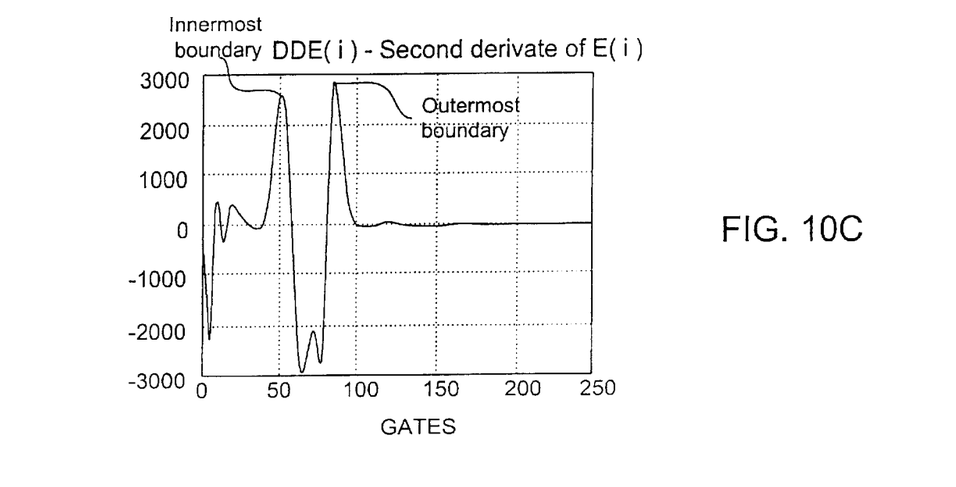

FIGS. 10A–10C illustrate the principles of another algorithm for boundary detection relating to the threshold technique, which involves analysis of the first and second derivatives $DE_i$ and $DDE_i$ (FIGS. 10B and 10C) of a function E(i) (shown in FIG. 10A) along the ultrasound beam. The dependence of the module of reflection signal on the gate coordinate, which is represented by the vector $E_i$, can be considered as a function of the reflection amplitude values E(i) along the beam (gates), i.e., E(i). The behavior of this function is irregular due to interference effects. To smooth the function E(i), the low passed filter is implemented. The smoothness of a signal can be also improved by additional averaging of E(i) on time, meaning that several vectors $E_i$ measured at successive moments of time are summed. The number of averaging defines the time interval during which the values $E_i$, and then the values of the chord L and diameter D, are calculated. This time interval can include one or several cardiocycles, or some particular time interval inside the cardiocycle, preferably systole or diastole. The corresponding chord value or vessel diameter for these cases will represent the averaged values for one cardiocycle or specifically systolic and diastolic values. In the example of FIG. 10A, the function E(i) is averaged on one cardiocycle, and then filtered.

To find the blood vessel boundaries, the algorithm first narrows the searching area. To this end, the initial and ending 10 gates are disregarded from consideration, because the values of function E(i) in these regions are changed by transient filter characteristics. For the innermost boundary, the algorithm defines the far limit of the searching area FIB as the gate number correspondent to the global maximum of the function E(i).

Then, the algorithm searches the last minimum of the function E(i), which is designated MIB in FIGS. 10A and 10B and which satisfies the following condition: $DE(i-1) \leq 0$, $DE(i) > 0$, where i=10, . . . , FIB. The innermost vessel boundary position is determined as the maximum of the second derivative DDE(i) within the interval i=MIB, . . . , FIB. As for the outermost boundary, the searching area is started from the global minimum of the second derivative DE(i), where i>FIB, and is ended at the gate number 210. The outermost boundary position is determined as the maximum of the second derivative DDE(i) of the function E(i), where FIB<i<210.

When the probe is correctly positioned with respect to the blood vessel, the processor 44 determines the beam inclination angles $\theta_1$ and $\theta_2$ using the conventional Doppler equation, on the assumption that an identical peak or average blood velocity is measured along both of the two ultrasound beams $B_1$ and $B_2$. Thereafter, based on the assumption at the blood vessel in the region of insonation has a circular cross section which changes in a radial fashion, the processor 44 continuously calculates the blood vessel's diameters $D_1$ and $D_2$ for the two ultrasound beams $B_1$ and $B_2$, respectively, according to the relationship: $D_1 = L_1 \sin\theta_1$ and $D_2 = L_2 \sin\theta_2$, and averages the results to be presented on the display 22. By this, the center of the blood vessel, and therefore the profile of the velocity in this central region, can be determined. Based on this measurement, the processor 44 calculates the blood flow measurement as the product of A and $v_{avg}$, where A is the blood vessel cross section area and $v_{avg}$ is the average blood flow speed. Alternatively, as shown in FIG. 11, the blood flow rate can be calculated by the integration algorithm as $\Sigma A_i v_i$, where $A_i$ is the semi-annular cross sectional area associated with a sample volume $SV_I$, and $v_i$ is the measured blood flow speed at a particular sample volume $SV_I$.

Finally, the processor 44 determines other blood flow information to be displayed as follows:

A time dependent distal resistance Rs(t) is determined according to the relationship:

$$Rs(t) = \frac{Pr(t)}{F(t)}$$

where Pr(t) is the time dependent arterial blood pressure Pr; and F(t) is the instantaneous blood flow.

a shear rate at the outermost surface $S_O$ and the innermost surface $S_I$ of the blood vessel's wall 34 with respect to the ultrasound probe is determined according to the relationship:

$$\frac{dV}{dD} \text{ at } D=0, \text{ and } D.$$

the blood vessel elasticity index is determined according to the relationship:

$$\frac{D_s - D_d}{D_d}$$

where $D_s$ is the blood vessel diameter at peak systole, and $D_d$ is the blood vessel diameter at diastole.

Those skilled in the art will readily appreciate that various modifications and changes can be applied to the embodiments of the invention as herein before exemplified without departing from its scope defined in and by the appended claims.

What is claimed is:

1. A measurement device including an ultrasonic transducer probe device for blood flow measurements in a patient's body, wherein:
    the probe device comprises a housing containing a transducer arrangement;
    the housing has an outer surface that is brought to a measurement location in the patient's body, said outer surface being patterned so as to have at least one projecting portion;
    said transducer arrangement comprises first and second ultrasound transducers, each operable in transmitting and receiving modes, the first and second transducers being oriented with respect to each other such that first and second ultrasound beams produced by the first and second transducers, respectively, propagate along first and second beam propagation axes intersecting at a certain acute angle;
    said projecting portion is configured, and located relative to said transducer arrangement, to position said transducer arrangement in a manner to enhance the accuracy of an ultrasound measurement; and
    the measurement device further comprises an indication means for providing an indication of blood flow measurement results.

2. The device according to claim 1, wherein the pattern on the outer surface of the housing is in the form of a tip-like projection, manipulation of the probe with respect to the patient's body enabling to displace a muscle layer above the blood vessel.

3. The device according to claim 1, wherein the pattern is in the form of two spaced-apart surface portions projecting from a recessed surface portion in the space between said two projecting surface portions, thereby enabling to locate a measurement location in a patient's blood vessel between the two projecting portions.

4. The device according to claim 3, wherein a size of the space between the two projecting portions is defined by a diameter of the blood vessel under measurement.

5. The device according to claim 3, wherein the transducer arrangement comprises two transducers, the pattern of said outer surface of the housing being such that a line connecting the two projecting portions is substantially perpendicular to a line between the two transducers.

6. The device according to claim 1, wherein the housing is a single-part unit with the patterned out surface thereof.

7. The device according to claim 6, wherein said first and second transducers are mounted inside the first part of the housing.

8. The device according to claim 1, wherein the housing has a two-part design comprising first and second parts, the second part being removably mountable onto the first part of the housing, the patterned outer surface of the housing being an outer surface of said second part.

9. A hand-held measurement device for ultrasound-based measurements of a blood flow in a patient's body, the measurement device utilizing the probe device constructed according to claim 1, and comprising a control unit connectable to the probe device, the probe device and the control unit being mounted in a common housing.

10. The device according to claim 9, wherein said control unit comprises an operation means for operating the probe during measurements, and an means for generating output data indicative of measurement results.

11. The device according to claim 9, wherein the measurements results are representative of a blood flow velocity waveform, determined by means of determination of chord values of the two beams and determination of a center of the chord.

12. The device according to claim 9, wherein said housing carrying the probe device and the control unit is shaped so as to be handled like a pen by a user during measurements.

13. A measurement device including an ultrasonic transducer probe device for non-invasive blood flow measurements in a patient's body, wherein:
    the probe device comprises a housing containing a transducer arrangement;
    the housing has an outer surface that is brought into contact with the patient's body, said outer surface being patterned so as to have a projecting tip-like portion that is configured to interact with body tissue during manipulation of the probe device with respect to the patient's body for enabling a muscle layer to be displaced above the measurement location;
    the transducer arrangement comprises first and second ultrasound transducers, each operable in transmitting and receiving modes, the first and second transducers being oriented with respect to each other such that first and second ultrasound beams produced by the first and second transducers, respectively, propagate along first and second beam propagation axes intersecting at a certain acute angle; and
    the measurement device further comprises an indication means for providing an indication of blood flow measurement results.

14. An ultrasound measurement device including a probe device for measuring a blood flow condition in a patient's blood vessel, wherein:
    the probe device comprises a housing containing a transducer arrangement;
    the housing is composed of first and second parts, the second part being removably mountable onto the first part, an outer surface of said second part, by which the probe is brought into contact with the blood vessel during measurements, having a pattern defining a recess for locating the blood vessel therein;
    said transducer arrangement comprises first and second ultrasonic transducers, each operable in transmitting and receiving modes, the first and second transducers being oriented with respect to each other such that first and second ultrasound beams produced by the first and second transducers, respectively, propagate along first and second beam propagation axes intersecting at a certain acute angle; and the measurement device further comprises an indication means for providing an indication of blood flow measurement results.

15. The device according to claim 14, wherein said first and second ultrasound transducers are mounted in the first part of the housing.

* * * * *